United States Patent
Milor et al.

(10) Patent No.: US 11,559,344 B2
(45) Date of Patent: *Jan. 24, 2023

(54) CLOSURE TOP DRIVER DEPTH LIMITER

(71) Applicant: Zimmer Spine S.A.S., Bordeaux (FR)

(72) Inventors: Pierre Milor, Limoges (FR); Bruno Ichelmann, Limoges (FR); Kevin Flaquiere, Barsac (FR)

(73) Assignee: Zimmer Spine, S.A.S.

( * ) Notice: Subject to any disclaimer, the term of this patent is extended or adjusted under 35 U.S.C. 154(b) by 255 days.

This patent is subject to a terminal disclaimer.

(21) Appl. No.: 17/012,780

(22) Filed: Sep. 4, 2020

(65) Prior Publication Data
US 2020/0397493 A1 Dec. 24, 2020

Related U.S. Application Data

(63) Continuation of application No. 16/014,069, filed on Jun. 21, 2018, now Pat. No. 10,792,084.
(Continued)

(51) Int. Cl.
*A61B 17/70* (2006.01)
*A61B 17/88* (2006.01)
(Continued)

(52) U.S. Cl.
CPC ...... *A61B 17/8875* (2013.01); *A61B 17/7091* (2013.01); *A61B 90/03* (2016.02);
(Continued)

(58) Field of Classification Search
CPC ............ A61B 17/7091; A61B 17/8875; A61B 17/888
See application file for complete search history.

(56) References Cited

U.S. PATENT DOCUMENTS

| 1,566,553 A | 12/1925 | Oliver et al. |
| 5,509,330 A | 4/1996 | Nick |
| (Continued) | | |

FOREIGN PATENT DOCUMENTS

| CA | 2831764 A1 | 5/2015 |
| CA | 2831764 C | 5/2015 |
| (Continued) | | |

OTHER PUBLICATIONS

"U.S. Appl. No. 16/014,069, Non Final Office Action dated Feb. 21, 2020", 10 pgs.
(Continued)

*Primary Examiner* — Nicholas W Woodall
(74) *Attorney, Agent, or Firm* — Sheridan Ross P.C.

(57) ABSTRACT

An apparatus to limit a seating depth of a fastener can include a cylindrical housing, a pin, a driver, and a biasing element. The cylindrical housing can include a proximal portion couplable to a tool, a distal portion engageable with a workpiece, and a bore extending from an opening on the distal portion towards the proximal portion along a longitudinal axis of the housing. The pin can be secured to the housing and can extend radially inward into the bore. The driver can be translatable within the bore of the housing and can extend beyond the opening on the distal portion to engage the fastener. The driver can include a slot that can be engageable with the pin to receive a torque from the pin and can rotate with the housing to transfer the torque to a fastener when the pin engages the slot.

20 Claims, 10 Drawing Sheets

Related U.S. Application Data

(60) Provisional application No. 62/523,405, filed on Jun. 22, 2017.

(51) Int. Cl.
  *A61B 90/00* (2016.01)
  *B25B 23/00* (2006.01)
  *B25B 23/10* (2006.01)
  *B25B 15/00* (2006.01)
  *B25B 21/00* (2006.01)

(52) U.S. Cl.
  CPC ........ *B25B 15/005* (2013.01); *B25B 23/0064* (2013.01); *B25B 23/108* (2013.01); *A61B 2090/035* (2016.02); *B25B 21/007* (2013.01); *B25B 23/0035* (2013.01)

(56) References Cited

U.S. PATENT DOCUMENTS

| | | |
|---|---|---|
| 5,682,800 A | 11/1997 | Jore |
| 5,746,298 A | 5/1998 | Krivec et al. |
| 6,021,694 A | 2/2000 | Beger |
| 6,439,086 B1 | 8/2002 | Bahr |
| 6,487,943 B1 | 12/2002 | Jansson et al. |
| 7,243,580 B2 | 7/2007 | Frazee |
| 7,334,509 B1 | 2/2008 | Gao |
| 7,735,400 B2 | 6/2010 | Chen |
| 7,861,623 B2 | 1/2011 | Miyazawa et al. |
| 9,931,739 B2 * | 4/2018 | Nelson .................... B25B 15/04 |
| 2004/0158247 A1 | 8/2004 | Sitiso et al. |
| 2009/0049961 A1 | 2/2009 | Chen |
| 2009/0126961 A1 | 5/2009 | Miyazawa et al. |
| 2010/0275746 A1 * | 11/2010 | Wengreen .......... A61B 17/8875 81/477 |
| 2015/0122089 A1 | 5/2015 | Rajotte |
| 2015/0201986 A1 | 7/2015 | Stank et al. |
| 2015/0202018 A1 | 7/2015 | Schaller et al. |
| 2018/0368902 A1 | 12/2018 | Milor et al. |

FOREIGN PATENT DOCUMENTS

| | | |
|---|---|---|
| JP | 2009125813 A | 6/2009 |
| JP | 5100325 B2 | 10/2012 |

OTHER PUBLICATIONS

"U.S. Appl. No. 16/014,069, Notice of Allowance dated Jun. 8, 2020", 5 pgs.

"U.S. Appl. No. 16/014,069, Response filed May 21, 2020 to Non Final Office Action dated Feb. 21, 2020", 13 pgs.

* cited by examiner

CLOSURE TOP DRIVER DEPTH LIMITER

CLAIM OF PRIORITY

This application is a continuation of U.S. patent application Ser. No. 16/014,069, filed on Jun. 21, 2018, which claims the benefit of U.S. Provisional Patent Application Ser. No. 62/523,405, filed on Jun. 22, 2017, the benefit of priority of each of which is claimed hereby, and each of which is incorporated by reference herein in its entirety.

BACKGROUND

A pedicle screw is a type of bone anchor designed for implant into a vertebral pedicle. Pedicle screws are often used together for rigid or semi-rigid (dynamic) fusion or stabilization of vertebrae. In many cases several adjacent vertebrae of the spinal region to be stabilized receive pedicle screws, where the pedicle screws support a connecting rod or connecting member. Once the pedicle screws are secured to the vertebrae the connecting member is positioned within the pedicle screws. To secure the connecting rod to the pedicle screws, closure tops are inserted (commonly threaded) into a distal portion of the pedicle screws to restrain the connecting member between the closure top and the pedicle screw.

OVERVIEW

The following, non-limiting examples, detail certain aspects of the present subject matter to solve the challenges and provide the benefits discussed herein, among others.

Example 1 describes an apparatus to limit a seating depth of a fastener. In this example, the apparatus can include a cylindrical housing, a pin secured to the housing, and a driver. The cylindrical housing can include a proximal portion, a distal portion, and a bore. The proximal portion can be coupled to a tool. The distal portion can be engaged with a workpiece, and the bore can extend from an opening on the distal portion towards the proximal portion along a longitudinal axis of the housing. The pin can be secured to the housing and extend radially inward into the bore. The driver can be translatable within the bore of the housing and extendable beyond the opening on the distal portion to engage the fastener. In this example, the driver can include a slot engageable with the pin to receive a torque from the pin and rotate with the housing to transfer the torque to a fastener when the pin engages the slot. The driver can also rotate relative to the housing when the pin does not engage the slot. The driver can also include a biasing element disposed within the bore to bias the driver distally.

In Example 2, the subject matter of Example 1 can include where the driver further includes a circumferential groove proximal to and adjacent the slot, where the circumferential groove is engageable with the pin to limit extension of the driver from the bore along the longitudinal axis and allow the driver to rotate relative to the housing when the slot is not engaged with the pin.

In Example 3, the subject matter of Example 2 can include where the driver is translatable within the bore along the longitudinal axis relative to the housing between a first position and a second position proximal of the first position, where the slot receives a torque from the pin when the driver is in the first position, and where the circumferential groove is engageable with the pin to allow the pin to rotate relative to the driver when the driver is in the second position.

In Example 4, the subject matter of Example 3 can include where the biasing element biases the driver towards the second position and is compressible to allow the driver to translate to the first position.

In Example 5, the subject matter of any one or more of Examples 2-4 can include where the driver further includes a pin stop distal of and adjacent the circumferential groove. The pin stop can limit distal translation of the driver relative to the housing.

In Example 6, the subject matter of any one or more of Examples 1-5 can include where the driver further includes a bit disposed on the distal end of the driver. The bit can be engageable with a fastener to turn the fastener as torque is transferred from the driver to the fastener, moving the fastener distally relative to the workpiece and allowing the driver to move towards the second position.

In Example 7, the subject matter of any one or more of Examples 1-6 can include a plurality of pins including the pin and a plurality of slots including the slot. The plurality of pins can be coupled to the housing, each extending radially inward. Each of the plurality of slots can be configured to receive any of the plurality of pins.

In Example 8, the subject matter of Example 7 can include where the plurality of pins includes a quantity of two pins, and where the plurality of slots comprises a quantity of at least four slots.

In Example 9, the subject matter of any one or more of Examples 1-8 can include where the pin is comprised of a geometric shape of a rectangular cuboid.

In Example 10, the subject matter of any one or more of Examples 1-9 optionally include the housing further comprising: a plurality of cleaning slots extending through a cylindrical sidewall of the housing into the bore.

In Example 11, the subject matter of any one or more of Examples 1-10 can include where the housing further includes a cavity in the distal portion configured to receive the fastener.

In Example 12, the subject matter of any one or more of Examples 1-11 can include where a depth of the slot determines the seating depth of the fastener.

Example 13 is an assembly for installing a closure top to a bone anchor, the assembly can include a bone anchor, a closure top, a tool, and a depth limiter. The bone anchor can be securable to a bone at a proximal end and open to receive a connecting member at a distal end. The closure top can be securable to the distal end of the bone anchor. The tool can be configured to deliver a torque to the closure top. The depth limiter can be coupled between the tool and the closure top. The depth limiter can include a cylindrical housing, a pin, a driver, and a biasing element. The cylindrical housing can include a proximal portion couplable to the tool, a distal portion engageable with the bone anchor, and a bore extending from the proximal portion through the distal portion along a longitudinal axis of the housing. The pin can be secured to the housing and can extend radially inward. The driver can be translatable within and extendable from the bore housing. The driver can include a slot engageable with the pin to receive a torque from the pin and rotate with the housing to transfer the torque to the closure top when the pin engages the slot. The driver can rotate relative to the housing when the pin does not engage the slot. The biasing element can be disposed within the bore to bias the driver distally.

In Example 14, the subject matter of Example 13 can include a cavity in the distal portion of the housing, where the cavity can form a proximal lip to engage the bone anchor, and the cavity can be configured to receive the closure top.

In Example 15, the subject matter of Example 14 can include where the lip of the distal portion engages the bone anchor allowing the biasing member to bias the driver distally, relative to the housing, as a torque is delivered from the driver to the closure top to move the closure top axially relative to the bone anchor.

In Example 16, the subject matter of any one or more of Examples 13-15 can include where the driver further includes a circumferential groove proximal to and adjacent the slot. The circumferential groove can be engageable with the pin to limit translation of the driver from the bore along the longitudinal axis, thereby limiting depth that the closure top extends into the bone anchor.

In Example 17, the subject matter of Example 16 can include where the driver is translatable within the bore along the longitudinal axis relative to the housing between a first position and a second position proximal of the first position, where the slot receives a torque from the pin when the driver is in the first position, and where the circumferential groove is engageable with the pin to allow the pin to rotate relative to the driver when the driver is in the second position.

In Example 18, the subject matter of Example 17 can include where the biasing element biases the driver towards the second position and is compressible to allow the driver to translate to the first position.

Example 19 is a method of installing a closure top in a bone anchor, the method can include the step of securing a bone anchor to a bone at a proximal end of the bone anchor. A closure top can engage a driver of a depth limiter. The closure top can engage the bone anchor. The driver can be moved to a first position where pins connected to a housing of the depth limiter engage slots of the driver by forcing a housing of the depth limiter to move distally relative to the driver against a biasing member within the housing. A torque can be applied to a tool coupled to the housing, where the torque can be transferred from the tool to the driver through the pins. The closure top can be rotated through continued application of the torque into the bone anchor causing the driver to extend distally relative to the housing into a second position where the pins disengage the slots preventing torque from being transferred to the driver.

In Example 20, the subject matter of any one or more of Examples 18-19 can include the step of discontinuing application of the torque when the driver reaches the second position and the pin disengages the slot and the driver stops transmitting the torque to the closure top.

Example 21 is a method of installing a closure top in a bone anchor, the method can include the step of securing a bone anchor to a bone at a proximal end of the bone anchor. A closure top can engage a driver of a depth limiter. The closure top can engage the bone anchor. The driver can be moved to a first position where pins connected to a housing of the depth limiter engage slots of the driver by forcing a housing of the depth limiter to move distally relative to the driver against a biasing member within the housing. A torque can be applied to a tool coupled to the housing, where the torque can be transferred from the tool to the driver through the pins. The closure top can be rotated through continued application of the torque into the bone anchor causing the driver to extend distally relative to the housing into a second position where the pins disengage the slots preventing torque from being transferred to the driver and limiting a depth that the closure top extends into the bone anchor.

In Example 22, the depth limiter, assembly, or method of any one of or any combination of Examples 1-21 is optionally configured such that all elements or options recited are available to use or select from.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

To secure connecting rods to pedicle screws, closure tops are commonly threaded into a distal portion of the pedicle screws to restrain the connecting member between the closure top and the pedicle screw. The closure tops are torqued as deemed appropriate by an installing physician. However, a torque that is too great may restrain movement of the connecting rod making later positioning of pedicle screws difficult. In some dynamic stabilization procedures, a torque that is too large may cause the closure top to compress the connecting member. If the connecting member is compressed by any of the closure tops in its system, proper tensioning of the connecting member may not be possible, and in some cases it may not be possible to apply any tension.

Because over-torqueing of closure tops may restrict the ability of a physician to tension a connecting member, physicians seek to avoid over-driving closure tops into pedicle screws. One common method used by physicians is haptic feedback or torque limiting created by resistance between a driven closure top and the connecting member. However, this method can apply pressure to the connecting member, where even a small about of pressure can impair proper tensioning of the connecting member. The inventors have recognized, among other things, that a depth limiter can be used to limit the depth at which a closure top is driven into a pedicle screw, helping to prevent closure tops from applying pressure to connecting members and allowing for proper tensioning of the connecting member.

The inventors have recognized that a depth limiter that is attachable to a tool can include a housing and one or more pins attached to the housing for transferring a torque to a driver, where the driver includes a bit or fastener interface. The driver can be translatable within the housing to transfer a torque from the tool to the fastener until the fastener reaches a predetermined depth. At this depth, the driver will be extended from the housing to a point that the pins disengage the driver and no longer transfer torque, thus preventing the fastener (or closure top) from being driven into a pedicle screw beyond a desired depth. The depth limiter, therefore, can prevent undesired pressure applied by the closure top to a connecting member within the pedicle screw, allowing proper completion of the procedure, including tensioning of the connecting member.

Figure 1:
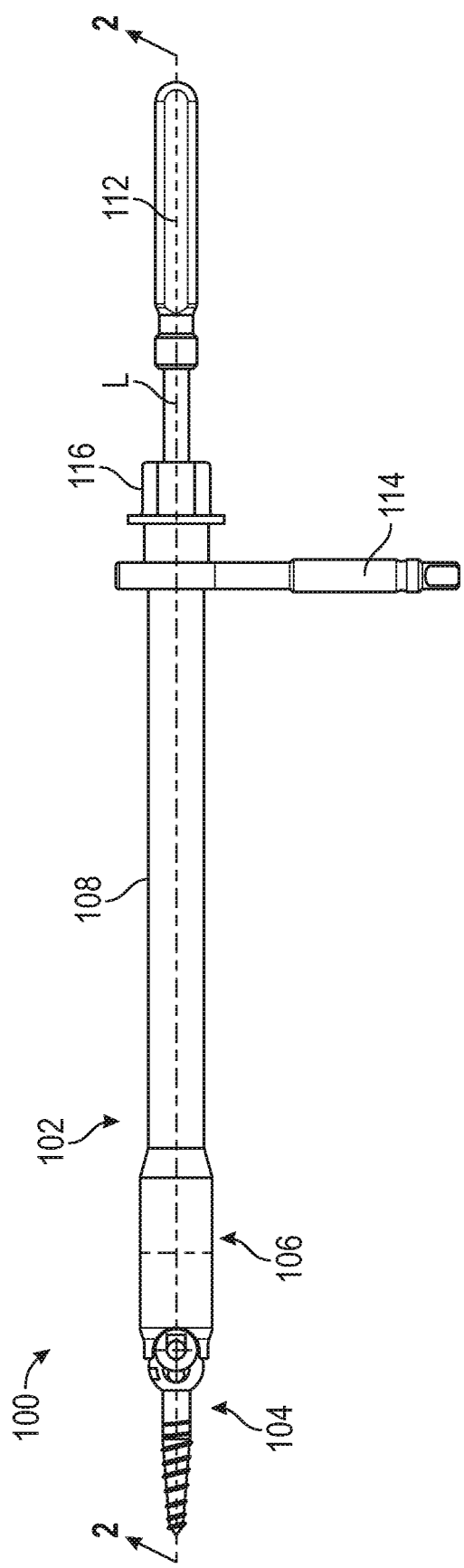
FIG. 1 illustrates a side view of a closure top installation assembly, in accordance with at least one example of this disclosure.
Figure 2:
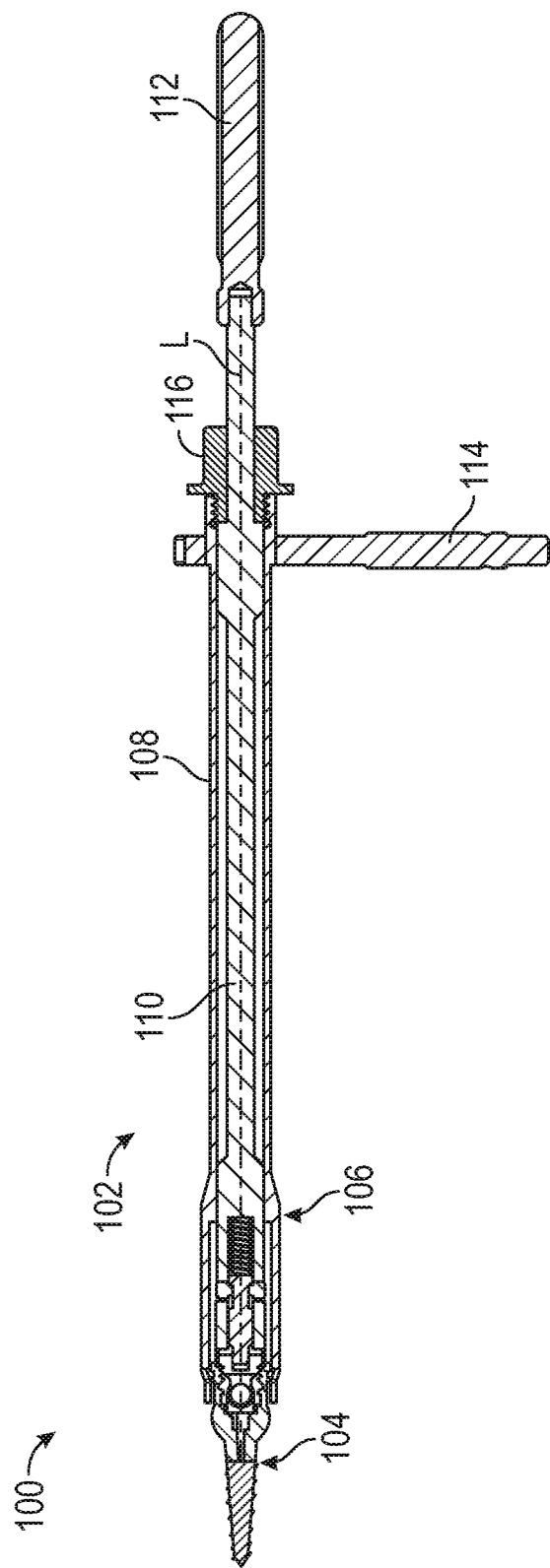
FIG. 2 illustrates a cross section view of the de closure top installation assembly across section 2-2 FIG. 1, in accordance with at least one example of this disclosure.

FIG. 1 illustrates a side view of closure top installation assembly 100, in accordance with at least one example of this disclosure. FIG. 2 illustrates a cross section view of closure top installation assembly 100 across section 2-2 of FIG. 1, in accordance with at least one example of this disclosure. FIGS. 1 and 2 are discussed below concurrently.

Closure top installation assembly 100 can include depth limiting tool 102 and bone anchor 104. Depth limiting tool 102 can include depth limiter 106, outer shaft 108, inner shaft 110, primary handle 112, secondary handle 114, and coupler 116. Also shown in FIG. 1 are section arrows 2-2. Also shown in FIGS. 1 and 2 are longitudinal axis L and orientation indicators Proximal and Distal.

Depth limiting tool 102 can be a tool configured for use during a surgical procedure of securing screws to bone. In some examples, depth limiting tool 102 can be configured to drive a bone anchor or pedicle screw into a vertebrae and can be also configured to secure a closure top to a proximal portion of the bone anchor to retain a connecting member or connecting rod within a head of the bone anchor. In operation of some examples, the depth limiting tool can include a depth limiter configured to selectively deliver torque to the closure top to effectively limit a depth at which the closure top can be inserted into the bone anchor. This provides the benefit of helping to avoid compression of the connecting member or rod between the closure top and the proximal portion of the bone anchor. Details of depth limiting tool 102 are further discussed below.

Bone anchor 104 can be an anchor configured to threadably engage and secure to bone. In some examples, bone anchor 104 can be a pedicle screw configured to secure to a pedicle of a vertebrae. Bone anchor 104 can be comprised of biocompatible materials such as metals, plastics, and combinations thereof.

Depth limiter 106 can be a device configured to limit a depth at which a closure top (not visible in FIG. 1) can be inserted into bone anchor 104, as discussed below in further detail. Depth limiter 106 can be connected to internal shaft 110, which can be a rigid shaft comprised of plastics, metals, or a combination thereof. Primary handle 112 can be a rigid device connected at a distal portion of primary handle 112 to a proximal portion of internal shaft 110. Primary handle can be configured to deliver a force to internal shaft 110. Internal shaft 110 can be capable of transferring a torque, in some examples, from primary handle 112 to depth limiter 106.

Outer shaft 108 can be a rigid shaft comprising an internal bore configured to house internal shaft 110. Outer shaft 108 can be comprised of plastics, metals, or a combination thereof. Secondary handle 114 can be coupled to outer shaft proximate a proximal termination of outer shaft 108. Outer shaft 108 can include a distal portion configured to engage bone anchor 104.

Coupler 116 can be a fastener, such as a nut, threadably engageable with an inner diameter of the bore of outer shaft 108 proximate the proximal termination of outer shaft 108. Coupler 116 can include a central bore coaxial with longitudinal axis L, the central bore receivable of inner shaft 110 therethrough, such that inner shaft 110 is rotatable within coupler 116 and independent of outer shaft 108.

In operation of one example, a distal portion of outer shaft 108 can engage a proximal portion of bone anchor 104. Secondary handle 114 can receive a torque and can transfer the torque through outer shaft 114 to thread bone anchor 104 into bone of a patient, for example.

Primary handle 112 can then be grasped while secondary handle 114 is used to stabilize outer shaft 108 relative to bone anchor 104. Primary handle 112 can be forced distally so that a driver of depth limiter 106 engages a closure top (which can be previously engaged with the driver). Primary handle 112 can then receive a torque, which can be transferred to depth limiter 106 through internal shaft 110. The driver of depth limiter 106 can deliver the torque to the closure top so that the closure top threads into a proximal portion of bone anchor 104. When the driver extends distally to a predetermine position as the driver translates with the closure top, the depth limiter will disengage from the driver so that torque cannot be transferred from primary handle 112 to the driver, thus limiting a depth at which the closure top can be driven into bone anchor 104. By limiting a depth at which the closure top can extend distally into bone anchor 104, depth limiter 106 helps to prevent the closure top from compressing a connecting member spanning between bone anchors, which can improve surgical procedural efficiency and patient quality of life.

Figure 3:
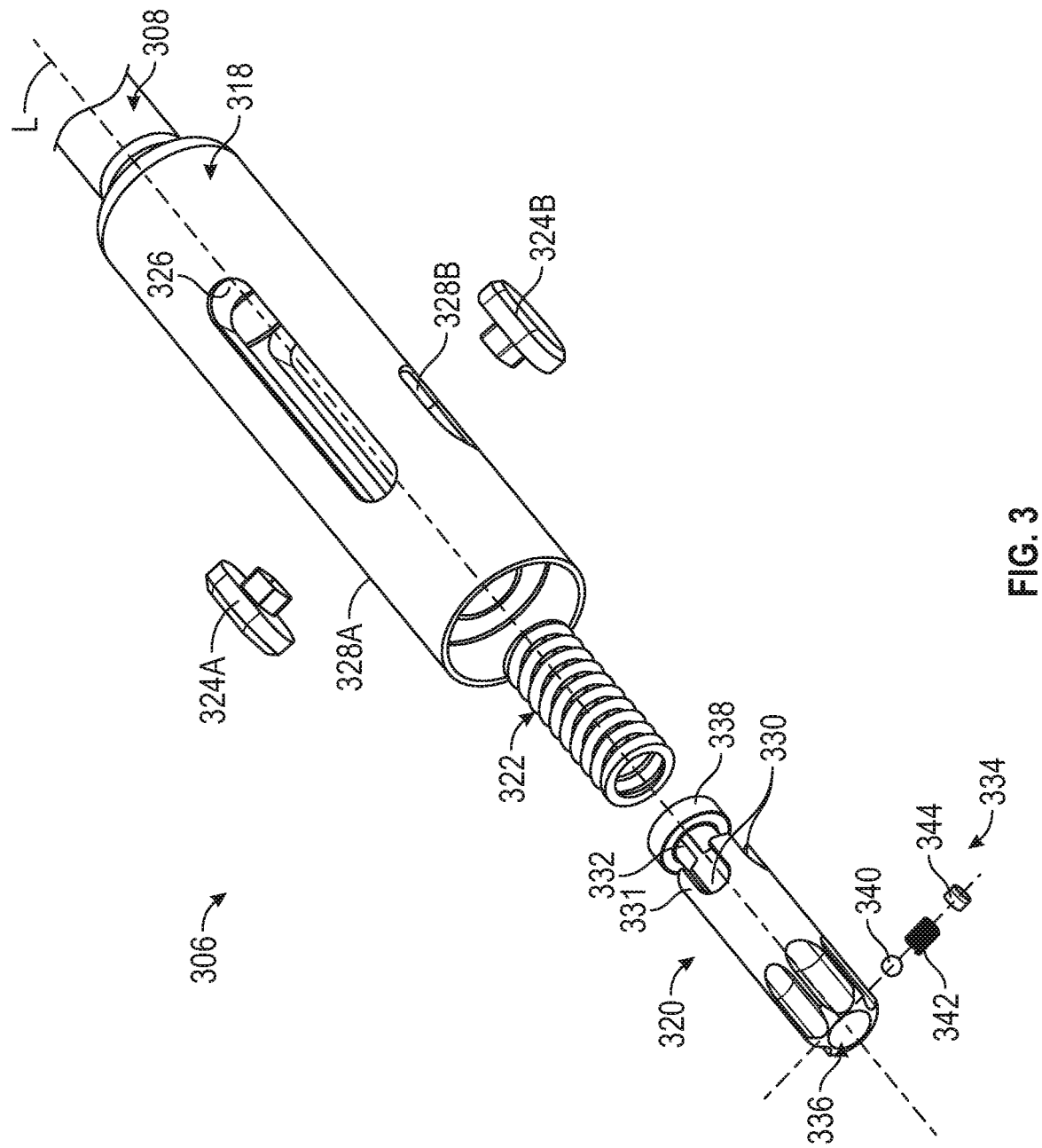
FIG. 3 illustrates an exploded isometric view of a depth limiter, in accordance with at least one example of this disclosure.

FIG. 3 illustrates an exploded isometric view of depth limiter 306, in accordance with at least one example of this disclosure. Depth limiter 306 can include housing 318, driver 320, biasing element 322, and pins 324A and 324B. Housing 318 can include cleaning slots 326 (one visible in FIG. 3) and pin slots 328 (328B visible and general location of 328A noted in FIG. 3). Driver 320 can include slots 330, axial extensions 331, circumferential groove 332, detent 334, bit 336, and pin stop 338. Detent 334 can include ball 340, detent bias 342, and detent cap 344. Also shown in FIG. 3 are longitudinal axis L and orientation indicators Proximal and Distal.

Housing 318 can be a cylindrical housing in some examples, but can be of other shapes in other examples, such as an octagonal prism. Housing 318 can be comprised of rigid materials, such as plastics, metals, and combinations thereof. Housing 318 can be coaxial with inner shaft 308 and can be connected to a distal portion of inner shaft 308 at a proximal portion of housing 318. Housing 318 can have two internal diameters, the smaller of which can be configured to receive biasing element 322 and driver 320, as further discussed below.

Cleaning slots 326 can extend along an outer surface of housing 318 and can extend through housing 318 to expose the inside of housing 318. Cleaning slots can have a circumferential dimension that is significantly smaller than an axial dimension allowing access to a majority of the components within housing 318 without limiting rigidity and therefore torque transferability of housing 318. Cleaning slots therefore can allow access to internal components of housing 318 for cleaning purposes. In some examples, the cleaning slots are omitted from housing 318, in these examples the device can be sealed or disassembled for cleaning as necessary.

Pin slots 328A and 328B can be sized to receive pins 324A and 324B, respectively. In some examples, pins 324A and 324B can be welded or otherwise permanently secured in pin slots 328A and 328B. Pins 324A and 324B can be pins insertable into pin slots 328A and 328B, extending into a central bore of housing 318, as shown in further detail below. Pins 324A and 324B can be comprised of rigid materials, such as plastics, metals, and combinations thereof.

Biasing element 322 can be a resilient member configured to bias driver 320 distally relative to housing 318. In some examples, biasing element can be a compression spring, such as a coil compression spring or a wave spring, in some examples. In some other examples, biasing element 322 can be other types of resilient members, such as a resilient plastic or rubber.

Driver 320 can be a rigid driver comprised of materials such as plastics, metals, and combinations thereof. Driver 320 can be sufficiently rigid to transfer a torque between proximal and distal portions of driver 320. Driver 320 can include bit 336 configured to interface with a closure at a distal portion of driver 320. In some examples, bit 336 can be a hexalobular internal (or star) interface, and can be other types of interfaces in other examples, such as cross-recess, standard slot, hexagonal, and the like. In certain examples, the bit 336 can be interchangeable to match the interface pattern of the closure. Driver 320 can also include a proximal portion that includes slots 330, circumferential groove 332, and pin stop 338, which can operate to selectively transfer torque from housing 318 to driver 320 to limit distal translation of driver 320 relative to housing 318, as discussed below.

Slots 330 can be slots or grooves extending radially inward from an outer surface of driver 320, and terminating prior to reaching an axial center of driver 320. Slots 300 also extend circumferentially and axially to form a shape configured to receive radial projections of pins 324A and 324B. Slots 330 can form axial extensions 331 between each of slots 330. Slots 330 can be of a quantity of four, as shown in FIG. 3, but can be of other quantities. For example, when two of pins 324A and 324B are used, slots 330 can be of any quantity allowing for symmetric placement of slots and allowing for space between slots, such as 2, 4, 6, 8, and the like. In some examples, there can be fewer or more pins and fewer or more slots.

Circumferential groove 332 can be a groove extending radially inward from an outer surface of driver 320, and terminating prior to reaching an axial center of driver 320. Circumferential groove 332 also extends the entire circumference of driver 320 and has an axial length. Circumferential groove 332 can form a shape configured to receive radial projections of pins 324A and 324B. Pin stop 338 can be located proximally adjacent to circumferential groove 332 and can be formed by circumferential groove 332. That is, circumferential groove 332 does not extend to a proximal axial termination of driver 320.

Detent 334 can be disposed within bit 336 to retain bit 336 to a closure top. Detent cap 344 can be fixedly disposed within a bore of bit 336, transverse to longitudinal axis L. Detent cap 344 can retain detent bias 342 and ball 340. Ball 340 can be a ball bearing, and the like, and can extend partially from bit 336 transversely to longitudinal axis L, where ball 340 is retained by a reduction in diameter of the transverse bore proximate an outer surface of bit 336.

Operations of some examples of depth limiter 306 are described with reference to FIGS. 4-9 Below.

Figure 4:
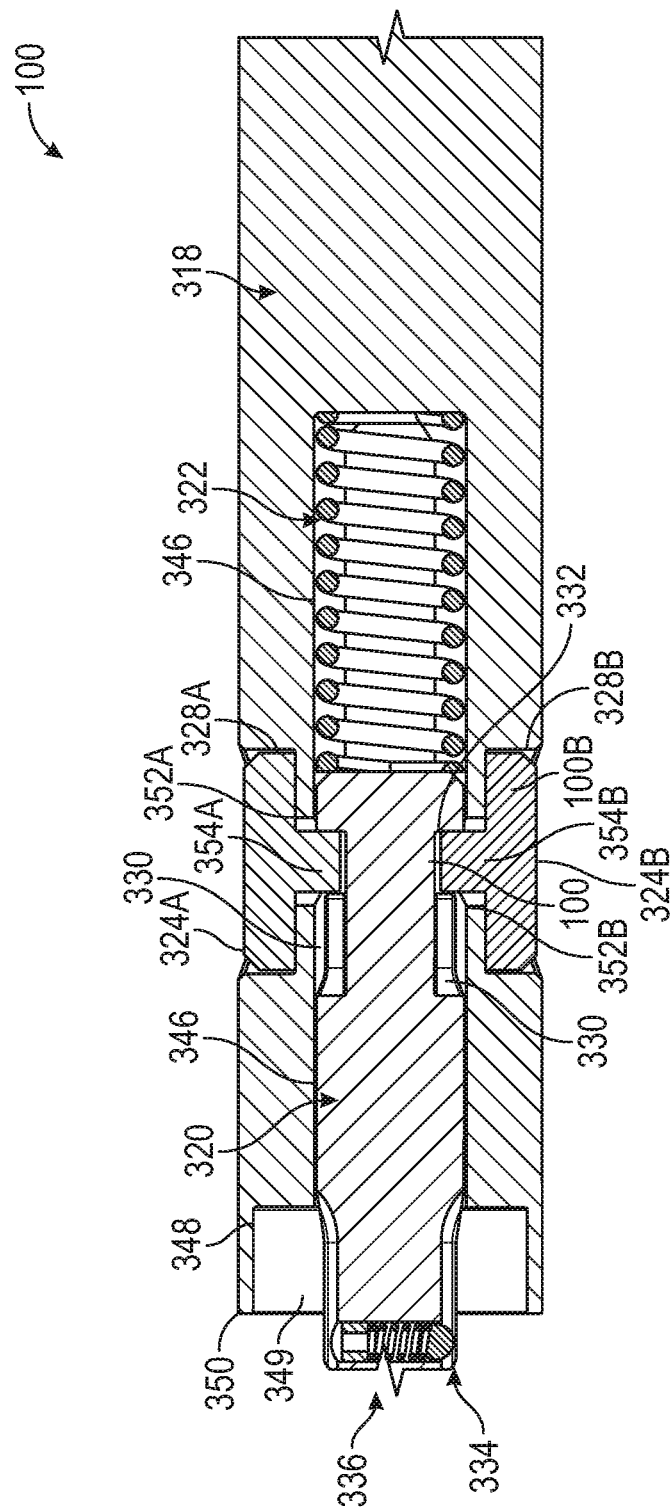
FIG. 4 illustrates a focused cross sectional view of a depth limiter, in accordance with at least one example of this disclosure.

FIG. 4 illustrates a focused cross sectional view of depth limiter 306 in a neutral position, in accordance with at least one example of this disclosure. Depth limiter 306 can include housing 318, driver 320, biasing element 322, and pins 324A and 324B. Housing 318 can include pin slots 328A and 328B, central bore 346, counterbore 348, distal cavity 349, and lip 350. Pin slots 328A and 328B can include pin bores 352A and 352B. Driver 320 can include slots 330, circumferential groove 332, detent 334, bit 336, and pin stop 338. Detent 334 can include ball 340, detent bias 342, and detent cap 344. Pins 324A and 324B can include radial extensions 354A and 354B. Also shown in FIG. 4 are orientation indicators Proximal and Distal.

Depth limiter 306 is consistent with FIGS. 1-3, except that FIG. 4 shows additional details of depth limiter 306, such as central bore 346, where biasing element 322 can be disposable within central bore 346 and can rest against a proximal termination of central bore 346. Driver 320 can also be disposable within central bore 346 so that a proximal termination of driver 320 rests against a distal termination of biasing element 322. Central bore 346 can be sized so that biasing element 322 and driver 320 can axially translate and rotate but cannot move transversely to the central longitudinal axis (shown in FIGS. 1-3).

FIG. 4 also shows pin bores 352A and 352B which can be sized to allow radial extensions 354A and 354B to extend radially inward to engage driver 320, but prevent a base of pins 324A and 324B from extending into internal bore 346. As shown in FIG. 4, when driver 320 is in a neutral position, radial extensions 354A and 354B rest in circumferential groove 332.

FIG. 4 further shows counterbore 348 which can extend proximally from a distal termination of housing 318 to create distal cavity 349 at the distal termination of housing 318 that surrounds driver 320. Distal cavity 349 can be sized to receive a closure top therein, as discussed below. The extension of counterbore 348 through the distal termination of housing 318 also creates lip 350, which can be a circumferential lip.

Figure 5:
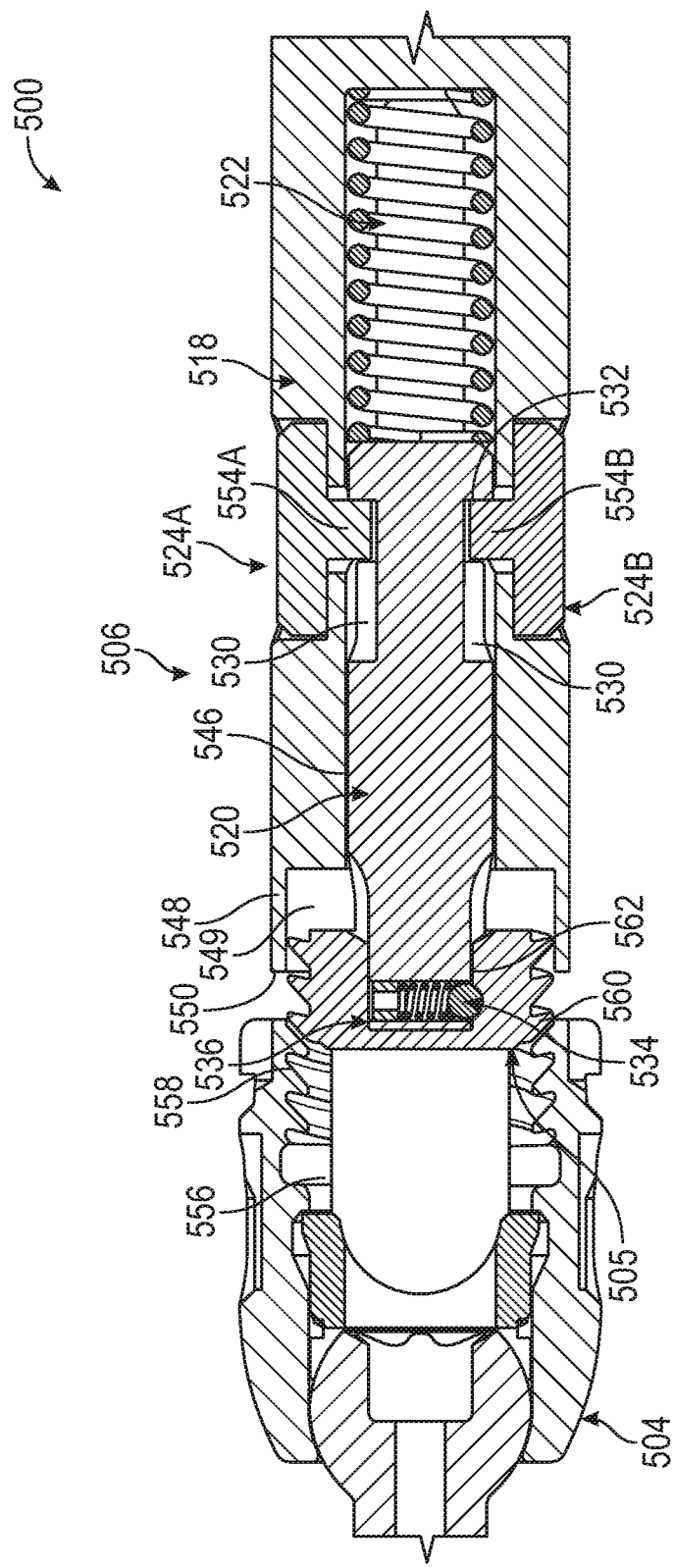
FIG. 5 illustrates a cross sectional view of a closure top installation assembly in a first position, in accordance with at least one example of this disclosure.

FIG. 5 illustrates a cross sectional view of closure top installation assembly 500 in a first position, in accordance with at least one example of this disclosure. Closure top installation assembly 500 can include bone anchor 504, closure top 505, depth limiter 506, and pins 524A and 524B. Depth limiter 506 can include driver 520 and housing 518. Housing 518 can include central bore 546, counterbore 548, distal cavity 549, and lip 550. Driver 520 can include bit 536 and detent 534. Bone anchor 504 can include anchor bore 556, which can include internal threaded portion 558. Closure top 505 can include external threaded portion 560 and tool interface 562. Also shown in FIG. 5 are orientation indicators Proximal and Distal.

Anchor bore 556 can be an axial bore extending distally from a proximal termination of bone anchor 504 partially into a head of bone anchor 504. Anchor bore 556 can include internal threaded portion 558 extending axially throughout a portion of anchor bore 556.

Closure top 505 can be a generally cylindrical rigid body comprised of metals, plastics, or a combination thereof. Closure top 505 can have an outer diameter complimentary with anchor bore 556. Closure top 505 can include external threaded portion 560, which can be sized to threadably engage internal threaded portion 558 of bone anchor 504. Closure top 505 can also include tool interface 562, which can be sized to receive bit 536 of driver 520.

In operation of some examples, driver 520 can be in a neutral position within housing 518, such that radial extensions 554A and 554B can be engaged with circumferential groove 532 of driver 520. Bit 536 can then be inserted into tool interface 562 of closure top 505, where detent 534 can engage tool interface 562 of closure top 505 to retain closure top 505 on driver 520. Driver 520 (by way of a handle and shaft, such as primary handle 112 and internal shaft 108 of FIGS. 1 and 2), can be used to align closure top 505 with anchor bore 556 of bone anchor 504, such that external threaded portion 560 aligns with internal threaded portion 558 of bone anchor 504. However, because radial extensions 554A and 554B of pins 524A and 524B, respectively, are disposed in circumferential groove 532, no torque can be transferred to closure top 505 to driver 520.

Figure 6:
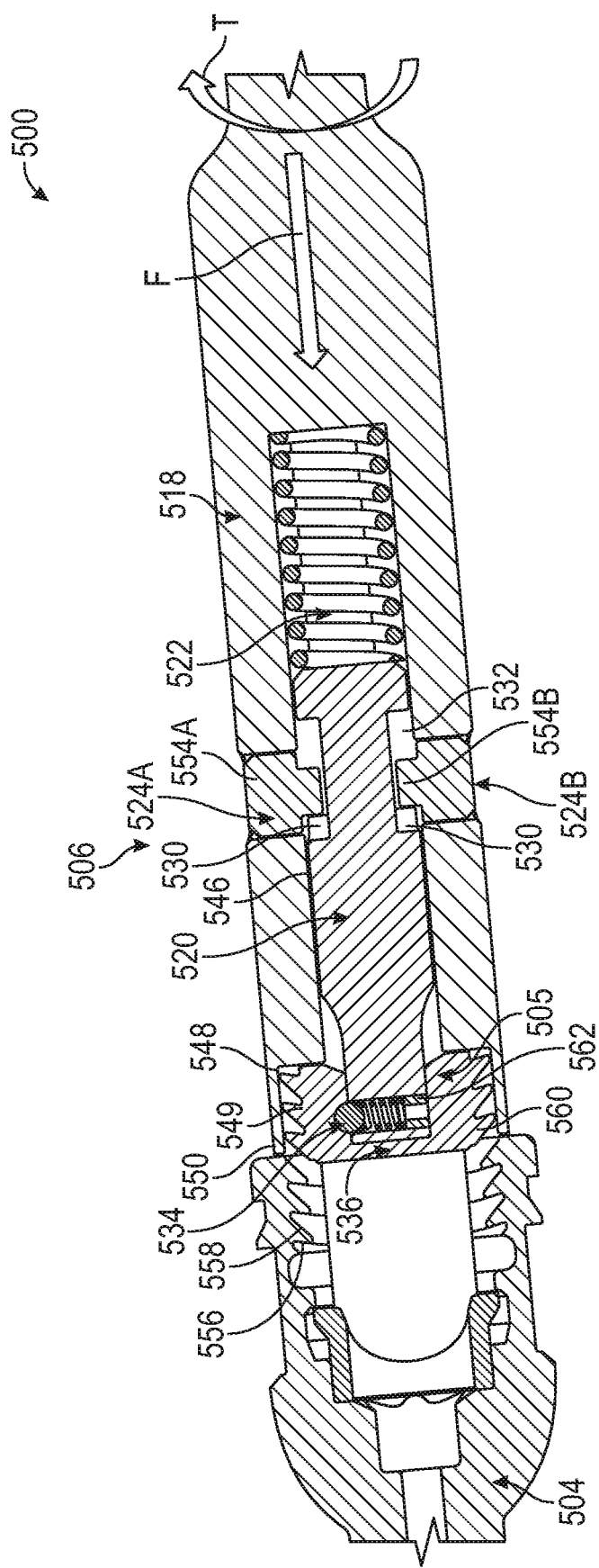
FIG. 6 illustrates a cross sectional view of a closure top installation assembly in a second position, in accordance with at least one example of this disclosure.

FIG. 6 illustrates a cross sectional view of a closure top installation assembly 500 in a second position, in accordance with at least one example of this disclosure. Closure top installation assembly 500 can include bone anchor 504, closure top 505, depth limiter 506, and pins 524A and 524B. Depth limiter 506 can include driver 520 and housing 518. Driver 520 can include bit 536 and detent 534. Bone anchor 504 can include anchor bore 556, which can include internal threaded portion 558. Housing 518 can include central bore 546, counterbore 548, distal cavity 549, and lip 550. Closure top 505 can include external threaded portion 560 and tool interface 562. Also shown in FIG. 6 are force F, torque T, and orientation indicators Proximal and Distal.

Once external threaded portion 560 is aligned with internal threaded portion 558, as shown in FIG. 5, force F can be applied axially to housing 518 (from inner shaft 108 and primary handle 112 of FIGS. 1 and 2, for example). Force F can cause housing 518 to translate distally until lip 550 contacts a proximal portion of bone anchor 504. Because closure top 505 is in contact with bone anchor 504, force F does not cause closure top 505 to translate with housing 518, causing housing 518 to move distally relative to driver 520, when force F is large enough to overcome a spring force of biasing member 522 (which opposes force F). As housing 518 moves relative to driver 520, driver 520 recedes proximally into central bore 546 and closure top 505 recedes proximally into distal cavity 549.

As driver 520 moves proximally into central bore 546, driver 520 moves relative to pins 524A and 524B. When driver 520 compresses biasing member 522 sufficiently, radial extensions 554A and 554B engage slots 530, as shown in FIG. 6. When radial extensions 554A and 554B are engaged with slots 530, torque T can be transferred from pins 524A and 524B to axial extensions (such as axial extensions 331 of FIG. 3) to driver 520. This allows driver 520 to transfer torque from bit 536 to tool interface 562 of closure cap 505, allowing closure cap 505 to rotate relative to bone anchor 504. In this way, closure cap 505 can be threaded by driver 520 into a proximal portion of bone anchor 504, as discussed further below.

Figure 7:
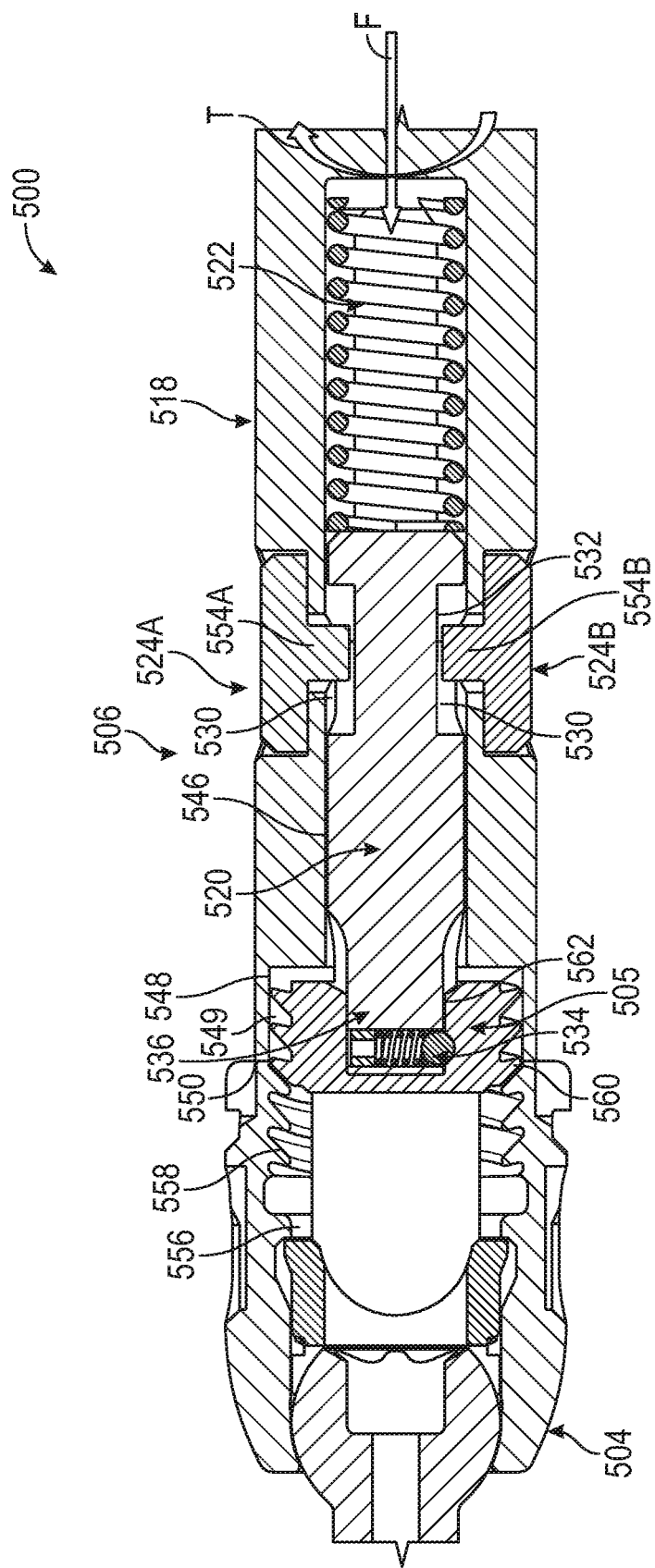
FIG. 7 illustrates a cross sectional view of a closure top installation assembly in a third position, in accordance with at least one example of this disclosure.

FIG. 7 illustrates a cross sectional view of closure top installation assembly 500 in a third position, in accordance with at least one example of this disclosure. Closure top installation assembly 500 can include bone anchor 504, closure top 505, depth limiter 506, and pins 524A and 524B. Depth limiter 506 can include driver 520 and housing 518. Driver 520 can include bit 536 and detent 534. Bone anchor 504 can include anchor bore 556, which can include internal threaded portion 558. Housing 518 can include central bore 546, counterbore 548, distal cavity 549, and lip 550. Closure top 505 can include external threaded portion 560 and tool interface 562. Also shown in FIG. 7 are force F, torque T, and orientation indicators Proximal and Distal.

As closure top 505 is threaded by driver 520 into a proximal portion of bone anchor 504, external threaded portion 560 begins to engage internal threaded portion 558. As closure top 505 extends into anchor bore 556, closure top 505 will begin to extend distally from 549 along with driver 520. This occurs, because lip 550 is in contact with bone anchor 504 and is prevented from extending distally with driver 520 and because driver 520 is biased to extend by biasing member 522 and is interlocked with closure top 505 by detent 534. Because driver 520 begins to extend distally from housing 518, driver 520 moves distally relative to radial extensions 554A and 554B of pins 524A and 524B, respectively. However, torque can still be transferred from housing 518 to driver 520 and therefore closure top 505 so long as radial extensions 554A and 554B of pins 524A and 524B engage slots 530 of driver 520.

Figure 8A:
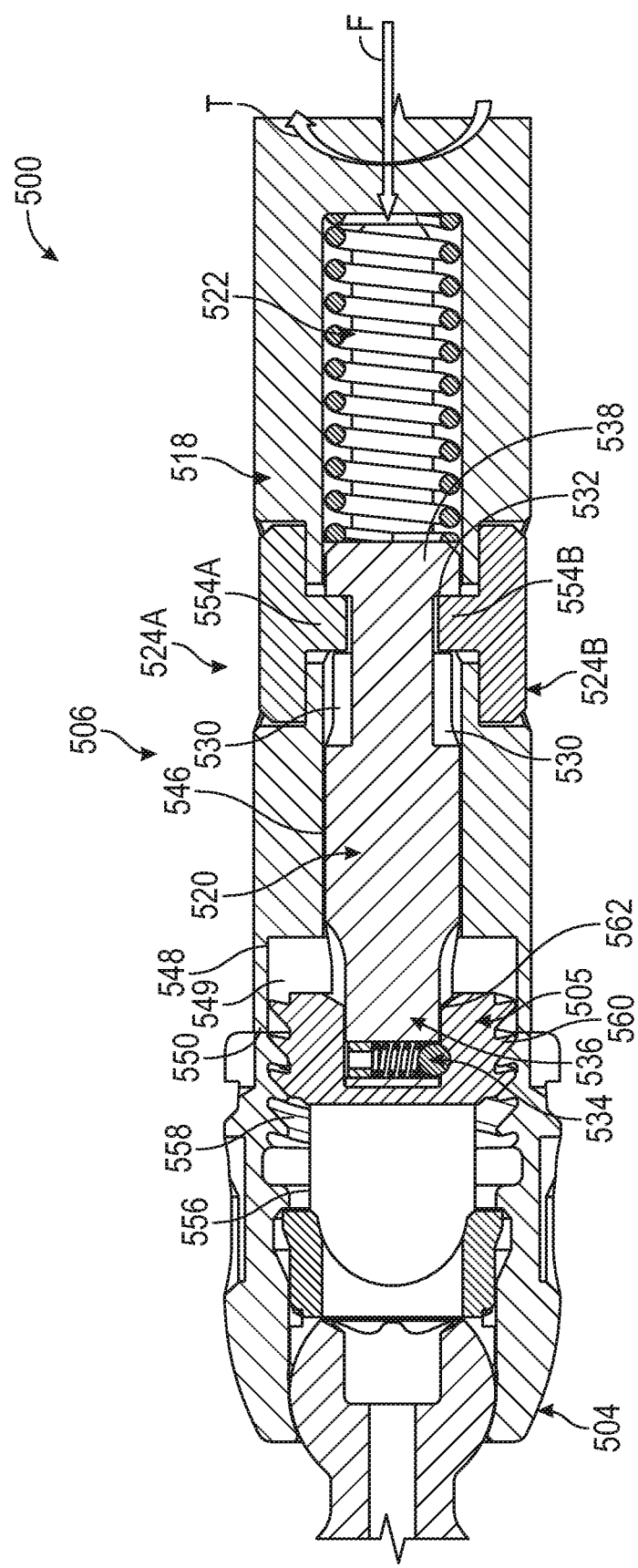
FIG. 8A illustrates a cross sectional view of a closure top installation assembly in a fourth position, in accordance with at least one example of this disclosure.
Figure 8B:
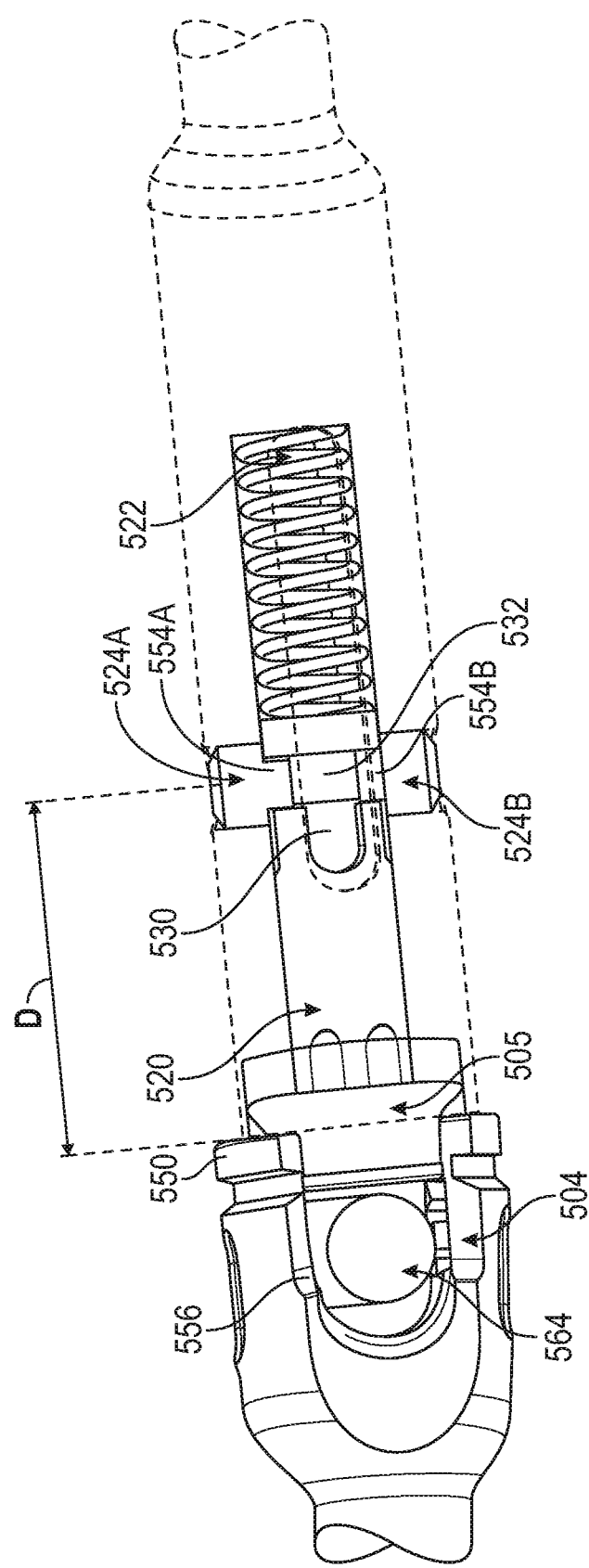
FIG. 8B illustrates an isometric view of a closure top installation assembly in a fourth position, in accordance with at least one example of this disclosure.

FIG. 8A illustrates a cross sectional view of closure top installation assembly 500 in a fourth position, in accordance with at least one example of this disclosure. FIG. 8B illustrates an isometric view of closure top installation assembly 500 in a fourth position, in accordance with at least one example of this disclosure. FIGS. 8A and 8B are discussed below concurrently.

Closure top installation assembly 500 can include bone anchor 504, closure top 505, depth limiter 506, pins 524A and 524B, and the components thereof as discussed above.

As closure top 505 is threaded further into bone anchor 504 by driver 520, closure top 505 and driver 520 distally extend further from housing 518, as shown in FIGS. 8A and 8B. This causes driver 520 to move distally relative to radial extensions 554A and 554B of pins 524A and 524B until radial extensions 554A and 554B reach circumferential groove 532. At this point, torque T can no longer be transferred from pins 524A and 524B because, circumferential groove 532 does not contact radial extensions 554A and 554B with any bodies that can receive an axial force or torque, and radial extensions 554A and 554B are no longer in contact with slots 530. As such, torque T will cause housing 518 to rotate relative to driver 520 when radial extensions 554A and 554B are positioned in circumferential groove 532. By preventing torque T from being transferred to driver 520, a depth at which closure top 505 can be inserted into bone anchor 504 is limited. This can provide the benefit of not over-torqueing or over tightening closure top 505 into bone anchor 504, which can help avoid reducing flexibility or movement of a connecting member or rod (such as connecting member 564) disposed within anchor bore 546. This can increase patient quality of life. Also, because depth limiting performed by depth limiter 506 is automatic, depth limiter 506 can increase procedural efficiency.

Also shown in FIGS. 8A and 8B is pin stop 538, which can contact radial extensions 554A and 554B of pins 524A and 524B when driver 520 is fully distally extended from housing 518 and radial extensions 554A and 554B reside in circumferential groove 532. This can prevent biasing element from forcing driver 520 to extend past a desired extension from housing 518 and can prevent driver 520 from falling out of housing 518.

FIG. 8B also shows distance D between lip 550 and pin 524A, which dictates a depth at which closure top 505 can be inserted into bone anchor 504. In some examples, pins 524A and 524B can be axially adjustable to increase or decrease D to decrease or increase the insertion depth of closure top 505. In some other examples, lip 550 can be adjustable to adjust the insertion depth of closure top 505. This can allow depth limiter to be used with multiple types of connecting members or rods, multiple bone anchor types, etc.

Figure 9:
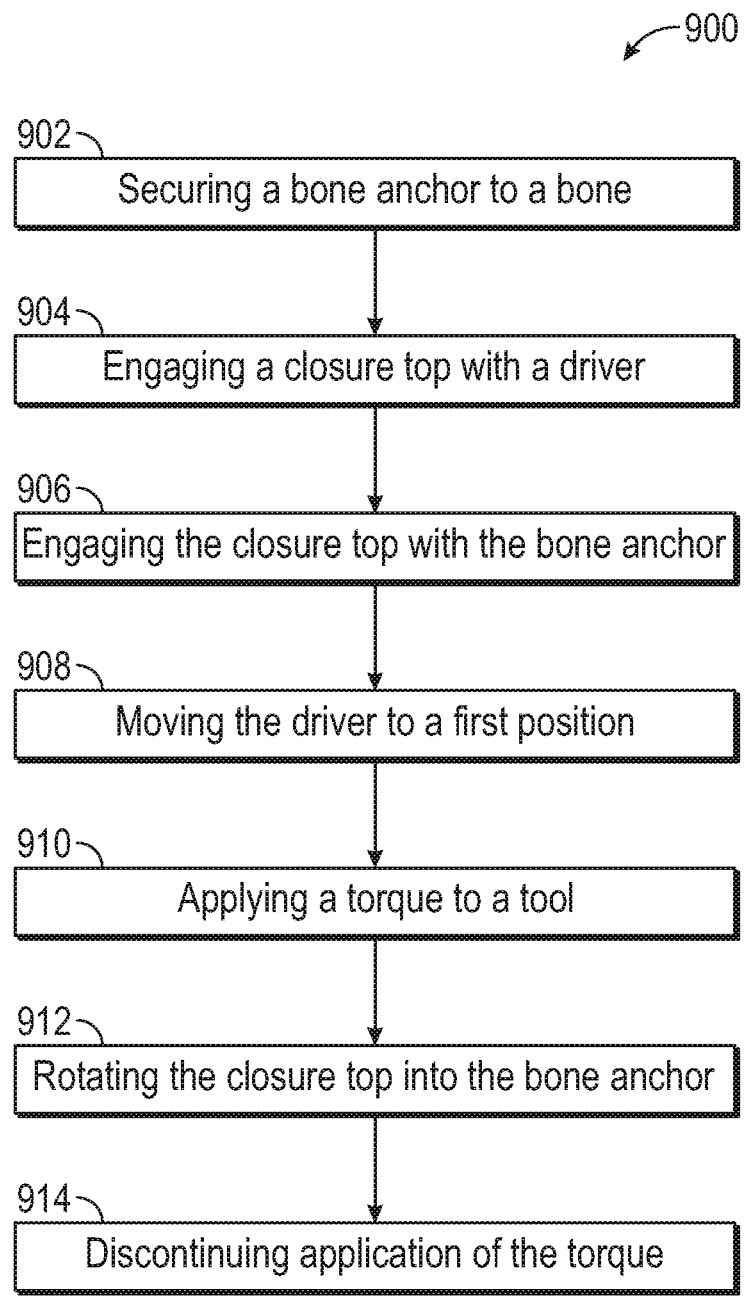
FIG. 9 illustrates a schematic of a method, in accordance with at least one example of this disclosure.

FIG. 9 illustrates a schematic of method 900, in accordance with at least one example of this disclosure. The steps or operations of method 900 are illustrated in a particular order for convenience and clarity; many of the discussed operations can be performed in a different sequence or in parallel without materially impacting other operations. Method 900 as discussed includes operations performed by multiple different actors, devices, and/or systems. It is understood that subsets of the operations discussed in method 900 attributable to a single actor, device, or system could be considered a separate standalone process or method. At step 902, method 900 can begin with securing a bone anchor to a bone using, for example, a depth limiting tool, such as depth limiting tool 102 of FIGS. 1 and 2. A connecting member can also be inserted into a head of the bone anchor at step 902 or otherwise prior to step 906.

At step 904, a driver of the depth limiting tool, such as driver 520 of FIG. 5, can be engaged with a closure top, such as closure top 505 of FIG. 5, in some examples. At step 906, the closure top can also be engaged with the bone anchor. A force (F) can then be applied to housing 518 of depth limiting tool 500, for example using handle 112, at step 908, to move driver 520 into a first position, such that pins 524A, 524B of housing 518 can engage slots 530 of driver 520.

At step 910, a torque (T) can be applied to the depth limiting tool 500, for example using handle 112, and can be transmitted via shaft 110 to housing 106 of depth limiting tool 100. Housing 106 can then transfer torque T via pins 524A and 534B to driver 520 so that driver 520 can rotate closure top 505, allowing closure top 505 to thread into internal threading of bone anchor 504, at step 912. As driver 520 rotates and extends from housing 506, driver 520 can disengage from pins 524A and 524B as pins 524A and 524B reach circumferential groove 5332 of driver 520. This can prevent further torque T from being transferred from housing 506 to driver 520 and therefore to closure top 505, effectively limiting a depth at which closure top 505 is inserted into bone anchor 504. As housing 506 spins freely relative to the driver 520, application of torque T can be discontinued at step 914.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such embodiments are entitled.

The invention claimed is:

1. An apparatus to limit a seating depth of a fastener:
   a cylindrical housing comprising a bore extending from an opening on a distal portion towards a proximal portion along a longitudinal axis of the cylindrical housing;
   a pin secured to the cylindrical housing and extending inward into the bore; and
   a driver translatable within the bore of the cylindrical housing and extendable beyond the opening on the distal portion to engage a fastener, the driver comprising:
   a slot engageable with the pin to receive a torque from the pin and rotate with the cylindrical housing to transfer the torque to the fastener when the pin engages the slot; and
   a circumferential groove proximal and adjacent the slot, the circumferential groove engageable with the pin to limit extension of the driver from the bore along the longitudinal axis and allow the driver to rotate relative to the cylindrical housing when the slot is not engaged with the pin.

2. The apparatus of claim 1, the driver further comprising:
a biasing element disposed within the bore to bias the driver distally.

3. The apparatus of claim 2, wherein:
the driver is translatable within the bore along the longitudinal axis relative to the cylindrical housing between a first position and a second position proximal of the first position; and
the slot receives a torque from the pin when the driver is in the first position; and
the circumferential groove is engageable with the pin to allow the pin to rotate relative to the driver when the driver is in the second position.

4. The apparatus of claim 3, wherein the biasing element biases the driver towards the second position and is compressible to allow the driver to translate to the first position.

5. The apparatus of claim 3, the driver further comprising a bit, the bit engageable with the fastener to turn the fastener as torque is transferred from the driver to the fastener.

6. The apparatus of claim 1, wherein the driver is rotatable relative to the cylindrical housing when the pin does not engage the slot.

7. The apparatus of claim 1, the driver further comprising a pin stop adjacent to the circumferential groove, the pin stop engageable with the pin to limit distal translation of the driver relative to the cylindrical housing.

8. The apparatus of claim 1, further comprising:
a plurality of pins including the pin, the plurality of pins coupled to the cylindrical housing, each extending radially inward into the bore; and
a plurality of slots including the slot, each of the plurality of slots configured to receive any of the plurality of pins.

9. The apparatus of claim 1, the cylindrical housing further comprising a cavity in the distal portion configured to receive the fastener.

10. The apparatus of claim 1, wherein a depth of the slot determines the seating depth of the fastener.

11. An assembly for installing a closure top to a bone anchor, the assembly comprising:
a bone anchor securable to a bone at a proximal end and open to receive a connecting member at a distal end;
a closure top securable to the distal end of the bone anchor;
a tool configured to deliver a torque to the closure top; and
a depth limiter comprising:
a cylindrical housing comprising a bore extending from and opening on a distal portion towards a proximal portion along a longitudinal axis of the cylindrical housing;
a pin secured to the cylindrical housing and extending inward into the bore; and
a driver translatable within the bore of the cylindrical housing and extendable beyond the opening on the distal portion to engage a fastener, the driver comprising:
a slot engageable with the pin to receive a torque from the pin and rotate with the cylindrical housing to transfer the torque to the fastener when the pin engages the slot; and
a circumferential groove proximal to and adjacent the slot, the circumferential groove engageable with the pin to limit extension of the driver from the bore along the longitudinal axis and allow the driver to rotate relative to the cylindrical housing when the slot is not engaged with the pin.

12. The assembly of claim 11, wherein the depth limiter further comprises a biasing element disposed within the bore to bias the driver distally.

13. The assembly of claim 12, wherein the biasing element biases the driver towards a second position and is compressible to allow the driver to translate to a first position.

14. The assembly of claim 11, wherein the assembly further comprises a cavity in the distal portion of the cylindrical housing, the cavity forming a proximal lip to engage the bone anchor, and the cavity configured to receive the closure top.

15. The assembly of claim 14, wherein the proximal lip of the distal portion engages the bone anchor allowing a biasing member to bias the driver distally, relative to the cylindrical housing, as a torque is delivered from the driver to the closure top to move the closure top axially relative to the bone anchor.

16. The assembly of claim 11, wherein:
the driver is translatable within the bore along the longitudinal axis relative to the cylindrical housing between a first position and a second position proximal of the first position;
the slot receives a torque from the pin when the driver is in the first position; and
the circumferential groove is engageable with the pin to allow the pin to rotate relative to the driver when the driver is in the second position.

17. An apparatus to limit a seating depth of a fastener:
a cylindrical housing comprising a bore extending from an opening on a distal portion towards a proximal portion along a longitudinal axis of the cylindrical housing;
a pin secured to the cylindrical housing and extending inward into the bore; and
a driver translatable withing the bore of the cylindrical housing and extendable beyond the opening on the distal portion to engage a fastener, the driver comprising:
a slot engageable with the pin to receive a torque from the pin and rotate with housing to transfer the torque to the fastener when the pin engages the slot;
a circumferential groove proximal to and adjacent the slot, the circumferential groove engageable with the pin to limit extension of the driver from the bore along the longitudinal axis and allow the driver to rotate relative to the cylindrical housing when the slot is engaged with the pin; and
a pin stop engageable with the pin to limit distal translation of the driver relative to the cylindrical housing.

18. The apparatus of claim 17, wherein the pin stop is adjacent to the circumferential groove.

19. The apparatus of claim 17, wherein the driver is rotatable relative to the cylindrical housing when the pin does not engage the slot.

20. The apparatus of claim 17, wherein a depth of the slot determines the seating depth of the fastener.

* * * * *